(12) United States Patent
Spottiswoode et al.

(10) Patent No.: US 10,109,050 B2
(45) Date of Patent: Oct. 23, 2018

(54) SPATIOTEMPORAL BACKGROUND PHASE CORRECTION FOR PHASE CONTRAST VELOCITY ENCODED MRI

(71) Applicants: Siemens Healthcare GmbH, Erlangen (DE); Northwestern University, Evanston, IL (US)

(72) Inventors: Bruce S. Spottiswoode, Chicago, IL (US); Michael Markl, Chicago, IL (US); Ning Jin, Powell, OH (US)

(73) Assignees: Siemens Healthcare GmbH, Erlangen (DE); Northwestern University, Evanston, IL (US)

( * ) Notice: Subject to any disclaimer, the term of this patent is extended or adjusted under 35 U.S.C. 154(b) by 113 days.

(21) Appl. No.: 15/169,861

(22) Filed: Jun. 1, 2016

(65) Prior Publication Data
US 2017/0352151 A1    Dec. 7, 2017

(51) Int. Cl.
*G06K 9/00*    (2006.01)
*G06T 7/00*    (2017.01)
(Continued)

(52) U.S. Cl.
CPC ............ *G06T 7/0012* (2013.01); *A61B 5/055* (2013.01); *A61B 5/725* (2013.01); *A61B 5/7207* (2013.01);
(Continued)

(58) Field of Classification Search
CPC ........ G01R 33/56316; G01R 33/56308; G01R 33/56518; G01R 33/56333; G01R 33/4824; G01R 33/561; G01R 33/5608; G01R 33/5616; G01R 33/5617; G01R 33/5611; G01R 33/5619; G01R 33/5602; G01R 33/56375; G01R 33/56383; G01R 33/5673; G01R 33/243; G01R 33/48;
(Continued)

(56) References Cited

U.S. PATENT DOCUMENTS

| 4,870,361 A | 9/1989 | In Den Kleef et al. |
| 6,535,620 B2 * | 3/2003 | Wildes ............... G06K 9/00335 382/107 |

(Continued)

OTHER PUBLICATIONS

Kerwin, W.S. et al., "Tracking MR Tag Surfaces Using a Spatiotemporal Filter and Interpolator", International Journal of Imaging Systems and Technology, vol. 10, issue 2 (Mar. 3, 1999), pp. 128-142.*
(Continued)

*Primary Examiner* — Jose Couso (57) ABSTRACT

A computer-implemented method for performing spatiotemporal background phase correction for phase contrast velocity encoded magnetic resonance imaging includes performing a phase contrast magnetic resonance imaging scan of a region of interest within a patient to yield a complex image and calculating a plurality of filter cut-off frequencies based on physiological limits associated with the patient. A spatiotemporal filter is created based on the plurality of filter cut-off frequencies. This spatiotemporal filter is applied to the complex image to yield a low-pass filtered complex image. Then, complex division is performed using the complex image and the low-pass filtered complex image to yield a corrected image.

20 Claims, 6 Drawing Sheets

(51) Int. Cl.
| | |
|---|---|
| G06K 9/46 | (2006.01) |
| G06T 7/20 | (2017.01) |
| G06T 5/00 | (2006.01) |
| A61B 5/055 | (2006.01) |
| A61B 5/00 | (2006.01) |
| G01R 33/563 | (2006.01) |
| G01R 33/565 | (2006.01) |
| A61B 5/113 | (2006.01) |

(52) U.S. Cl.
CPC . G01R 33/56316 (2013.01); G01R 33/56509 (2013.01); G01R 33/56518 (2013.01); G06K 9/4671 (2013.01); G06T 5/00 (2013.01); G06T 7/20 (2013.01); A61B 5/113 (2013.01); G06K 2009/4666 (2013.01); G06T 2207/10088 (2013.01); G06T 2207/20024 (2013.01); G06T 2207/30004 (2013.01)

(58) Field of Classification Search
CPC ............ G01R 33/4816; G01R 33/4826; G01R 33/4833; G01R 33/56; G01R 33/4804; G01R 33/5601; G01R 33/563; G01R 33/56341; G01R 33/5659; G01R 33/58; G01R 33/32; G01R 33/445; G01R 33/4828; G01R 33/565; G01R 33/56536; A61B 5/055; A61B 5/0263; A61B 5/7285; A61B 5/0044; A61B 5/0402; A61B 5/0033; A61B 5/7207; A61B 6/032; A61B 6/037; A61B 8/43; A61B 8/5223; G06T 7/0012; G06T 7/20; G06T 5/00; G06T 5/50; G06T 11/003; G06T 11/006; G06T 7/277; G06T 7/215; G06T 7/11; G06T 2207/10088–2207/10096; G06T 2207/20221; G06T 2207/30016; G06T 2207/30048; G06T 2207/30101; G06T 2207/30004; G06T 2210/41; G06K 9/4671; G06K 9/3216; G06K 9/00496; G06K 2209/05; A61N 7/02; H04N 19/51; Y10S 128/922

See application file for complete search history.

(56) References Cited

U.S. PATENT DOCUMENTS

| | | | | |
|---|---|---|---|---|
| 6,892,089 | B1* | 5/2005 | Prince | A61B 5/055 |
| | | | | 128/922 |
| 7,317,841 | B2* | 1/2008 | Yatsenko | G06T 5/002 |
| | | | | 382/260 |
| 7,755,355 | B2 | 7/2010 | Polzin | |
| 7,831,088 | B2* | 11/2010 | Frakes | G06K 9/3216 |
| | | | | 382/154 |
| 9,326,748 | B2* | 5/2016 | Sumi | A61B 8/08 |
| 2007/0003121 | A1* | 1/2007 | Aach | G06T 7/0012 |
| | | | | 382/130 |
| 2017/0059682 | A1* | 3/2017 | Dagher | G01R 33/243 |

OTHER PUBLICATIONS

Bernstein, Mat A., et al. "Concomitant gradient terms in phase contrast MR: analysis and correction." Magnetic resonance in medicine 39.2 (1998): 300-308.

Busch, Julia, et al. "Analysis of temperature dependence of background phase errors in phase-contrast cardiovascular magnetic resonance." Journal of Cardiovascular Magnetic Resonance 16:97 (2014): 1-12.

Gatehouse, Peter D., et al. "Flow measurement by cardiovascular magnetic resonance: a multi-centre multi-vendor study of background phase offset errors that can compromise the accuracy of derived regurgitant or shunt flow measurements." Journal of Cardiovascular Magnetic Resonance 12:5 (2010): 1-8.

Kadbi, Mo, et al. "4D UTE flow: a phase-contrast MRI technique for assessment and visualization of stenotic flows." Magnetic resonance in medicine 73.3 (2015): 939-950.

Lankhaar, Jan-Willem, et al. "Correction of phase offset errors in main pulmonary artery flow quantification." Journal of Magnetic Resonance Imaging 22.1 (2005): 73-79.

Markl, Michael, et al. "Time-resolved 3D MR velocity mapping at 3T: Improved navigator-gated assessment of vascular anatomy and blood flow." Journal of magnetic resonance imaging 25.4 (2007): 824-831.

Rolf, Marijn P., et al. "Sequence optimization to reduce velocity offsets in cardiovascular magnetic resonance volume flow quantification-A multi-vendor study." Journal of Cardiovascular Magnetic Resonance 13:18 (2011): 1-10.

Uppman, M., et al. "Background phase correction using k-space filters in phase contrast velocity encoded MRI." Proc. Intl. Soc. Mag. Reson. Med. 18 (2010): 3075.

Wang, Y., et al. "Artery and vein separation using susceptibility-dependent phase in contrast-enhanced MRA." Journal of Magnetic Resonance Imaging 12.5 (2000): 661-670.

\* cited by examiner

SPATIOTEMPORAL BACKGROUND PHASE CORRECTION FOR PHASE CONTRAST VELOCITY ENCODED MRI

TECHNOLOGY FIELD

The present invention relates generally to methods, systems, and apparatuses for performing spatiotemporal background phase correction for phase contrast velocity encoded Magnetic Resonance Imaging (MRI) applications.

BACKGROUND

In Phase Contrast Magnetic Resonance Imaging (PC-MRI), background phase offsets occur due to eddy currents and concomitant gradient terms, which can introduce substantial errors in the velocity measurements. A number of steps can be taken to minimize these errors, but background phase errors still remain and the accuracy of the PC-MRI techniques often fails to meet clinical needs for integrated flow measurements. Two solutions to compensate for residual eddy currents are to perform a separate phantom scan with the same sequence, imaging parameters, orientation, and scan location, or to physically measure the magnetic field during the scan. Both of these methods require additional time on the scanner, and do not compensate for errors specific to the anatomy being imaged. Furthermore, eddy current induced phase offsets may not be sufficiently stable over time for correction methods using separate measurements to work effectively.

Phase correction can alternatively be performed as a post-processing step. The most common post processing correction technique involves estimating the phase variation in stationary tissue and subtracting a fitted surface, typically polynomials or basis functions. Previous work shows that a high order polynomial may be beneficial. An alternative technique, used in susceptibility weighted imaging, is to assume that the phase inhomogeneities are low frequencies in k-space and can be filtered out using a high-pass k-space filter. In practice, this can be implemented by performing a complex division of the original image and a low-pass filtered version of the original image. This approach has been applied previously for PC-MRI, but only using the spatial dimensions.

SUMMARY

Embodiments of the present invention address and overcome one or more of the above shortcomings and drawbacks, by providing methods, systems, and apparatuses related to performing spatiotemporal background phase correction for phase contrast velocity encoded MRI applications. In contrast to conventional technique, PC MRI measurements are exploited in the temporal dimension or additional spatial dimensions. Such measurements are almost exclusively time resolved, i.e. multiple time points during the cardiac cycle, and may be acquired as 3D volumes and not just 2D slices.

According to some embodiments, a computer-implemented method for performing spatiotemporal background phase correction for phase contrast velocity encoded magnetic resonance imaging includes performing a phase contrast magnetic resonance imaging scan of a region of interest within a patient to yield a complex image and calculating a plurality of filter cut-off frequencies based on physiological limits associated with the patient. A spatiotemporal filter is created based on the plurality of filter cut-off frequencies. This spatiotemporal filter is applied to the complex image to yield a low-pass filtered complex image. Then, complex division is performed using the complex image and the low-pass filtered complex image to yield a corrected image.

In some embodiments of the aforementioned method, the cut-off frequencies are calculated based on a flow profile through a vessel of interest present in the complex image. For example, in one embodiment, the filter cut-off frequencies in the spatial domain are specified with the lowest allowable frequency corresponding to twice the diameter of a largest vessel lumen as measured in pixels. The filter cut-off frequencies in the temporal domain may be specified to remove all motion except for bulk motion of the patient in the region of interest. For example, where the bulk motion of the patient in the region of interest is due to respiration, the filter cut-off frequencies in the temporal domain may be specified using the frequency of the patient's respiratory cycle.

The application of the spatiotemporal filter to the complex image to yield a low-pass filtered complex image may vary according to different embodiments. For example, in one embodiment, the spatiotemporal filter is in the frequency domain and the complex image is multiplied with a filtering kernel corresponding to the spatiotemporal filter to yield the low-pass filtered complex image. In another embodiment, a spatiotemporal filter in the spatial domain is applied to the complex image by performing a convolution of a filtering kernel corresponding to the spatiotemporal filter and the complex image. In still other embodiments, a spatiotemporal filter in the temporal domain is applied to the complex image by performing a convolution of a filtering kernel corresponding to the spatiotemporal filter and the complex image.

The aforementioned method may be supplemented with additional features further refining the claimed technique. For example, in one embodiment, the spatiotemporal filter comprises a first filter in the temporal domain and a second filter in the spatial domain which is independent from the temporal filter. In another embodiment, the phase contrast magnetic resonance imaging scan is performed in a plurality of spatial dimensions and 1 temporal dimension. The spatiotemporal filter may then be applied to the complex image in each spatial dimension.

According to another aspect of the present invention, an article of manufacture for performing spatiotemporal background phase correction for phase contrast velocity encoded magnetic resonance imaging comprises a non-transitory, tangible computer-readable medium holding computer-executable instructions for performing the aforementioned method, with or without the additional features set out above.

According to other embodiments of the present invention, a system for performing spatiotemporal background phase correction for phase contrast velocity encoded magnetic resonance imaging comprises a magnetic resonance imaging scanner and a computer comprising an image data processor. The magnetic resonance imaging scanner is configured to perform a phase contrast magnetic resonance imaging scan of a region of interest within a patient to yield a complex image. The image data processor is configured to calculate filter cut-off frequencies based on physiological limits associated with the patient; create a spatiotemporal filter based on the cut-off frequencies; apply the spatiotemporal filter to the complex image to yield a low-pass filtered complex image; and perform complex division using the complex image and the low-pass filtered complex image to yield a corrected image. In some embodiments, the image data processor may be further configured to identify a vessel of interest present in the complex image and the cut-off frequencies may be calculated based on a flow profile through the vessel of interest using techniques which are similar to the methods discussed above.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to performing spatiotemporal background phase correction for phase contrast velocity encoded MRI applications. More specifically, the techniques described herein improve the correction for background phase offset errors for phase contrast velocity encoded MRI, or PC-MRI, which measures fluid (blood, CSF) or tissue velocities at multiple time points during the cardiac cycle using the phase of a complex magnetic resonance (MR) image. Phase errors due to eddy currents commonly still exist despite performing a phase reference scan, using gradient pre-emphasis, protocol optimization, correcting for Maxwell terms, and performing retrospective phase correction. These errors manifest as spatially variant biases in the phase images. With the techniques described herein, spatiotemporal filters are used as an improvement over existing retrospective phase correction techniques. Filter settings are based on physiologically meaningful parameters such as vessel diameter and respiratory frequency.

Figure 1:
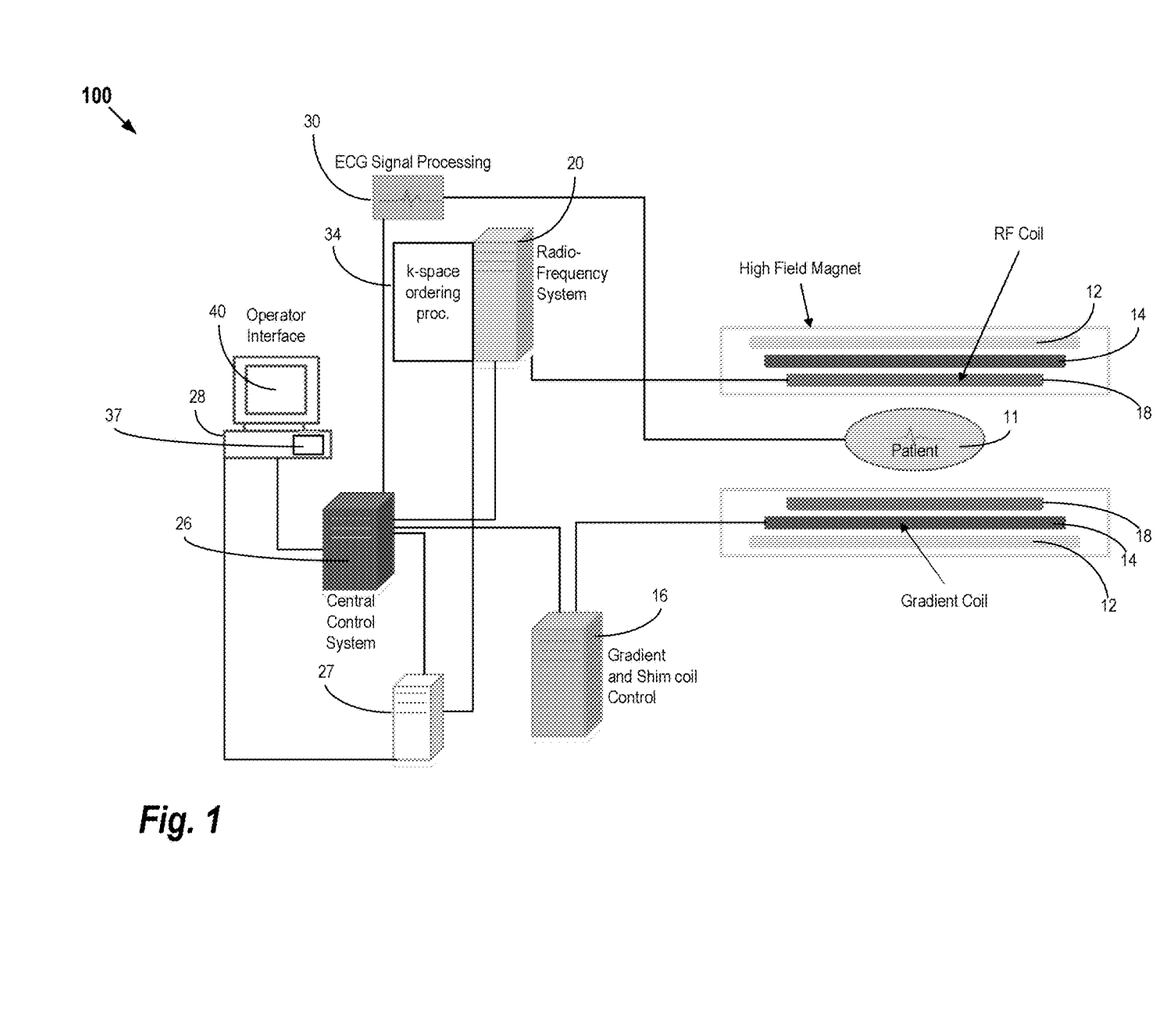
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing magnetic resonance imaging (MRI) data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components which are substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques generally known in the art may be used for reconstruction.

The residual background phase errors in PC-MRI, largely due to eddy currents, typically do not vary much as a function of time during the cardiac cycle. Conventional methods which utilize surface fitting routinely identify stationary tissue as having a low temporal standard deviation. However, depending on the anatomy, the distribution of the stationary tissue in the image is often insufficient for reliable high order (i.e., nonlinear) surface fitting. Filtering in the frequency domain, on the other hand, is not dependent on the area and distribution of stationary tissue.

The velocity measurements in a particular vessel may be adversely affected with incorrect high order surface fitting, or with incorrect cutoff frequency selection when using a frequency domain filter. The low-pass spatial filter cutoff frequency should be high enough to adequately describe the residual phase errors due to eddy currents, but not so high as to modify the velocity profile through the vessel of interest. In practice, this may be difficult to achieve for certain anatomical locations and flow containing vessels, and there is, thus, a tradeoff between adequate background phase correction and adversely affecting the flow measurement. Assuming limited bulk motion in the image during the cardiac cycle, a low-pass temporal frequency filter can also be applied to eliminate phase values which change rapidly through time. By using a spatiotemporal filter, a lower cutoff frequency can be used in the spatial domain while still achieving sufficient background phase correction.

Such a spatiotemporal filter may be generated in a variety of ways. For example, in some embodiments, the spatiotemporal filter is generated in the frequency domain using multiplication with an appropriate kernel (e.g., a Gaussian or Hanning profile). In other embodiments, the spatiotemporal filter is implemented in the spatial/temporal domain using convolution with an appropriate kernel (for example, a Gaussian or Hanning profile). In still other embodiments, an independent temporal filter is applied, followed by a spatial filter. For example, a median filter may be applied in the temporal domain, followed by a spatial filter.

Figure 2:
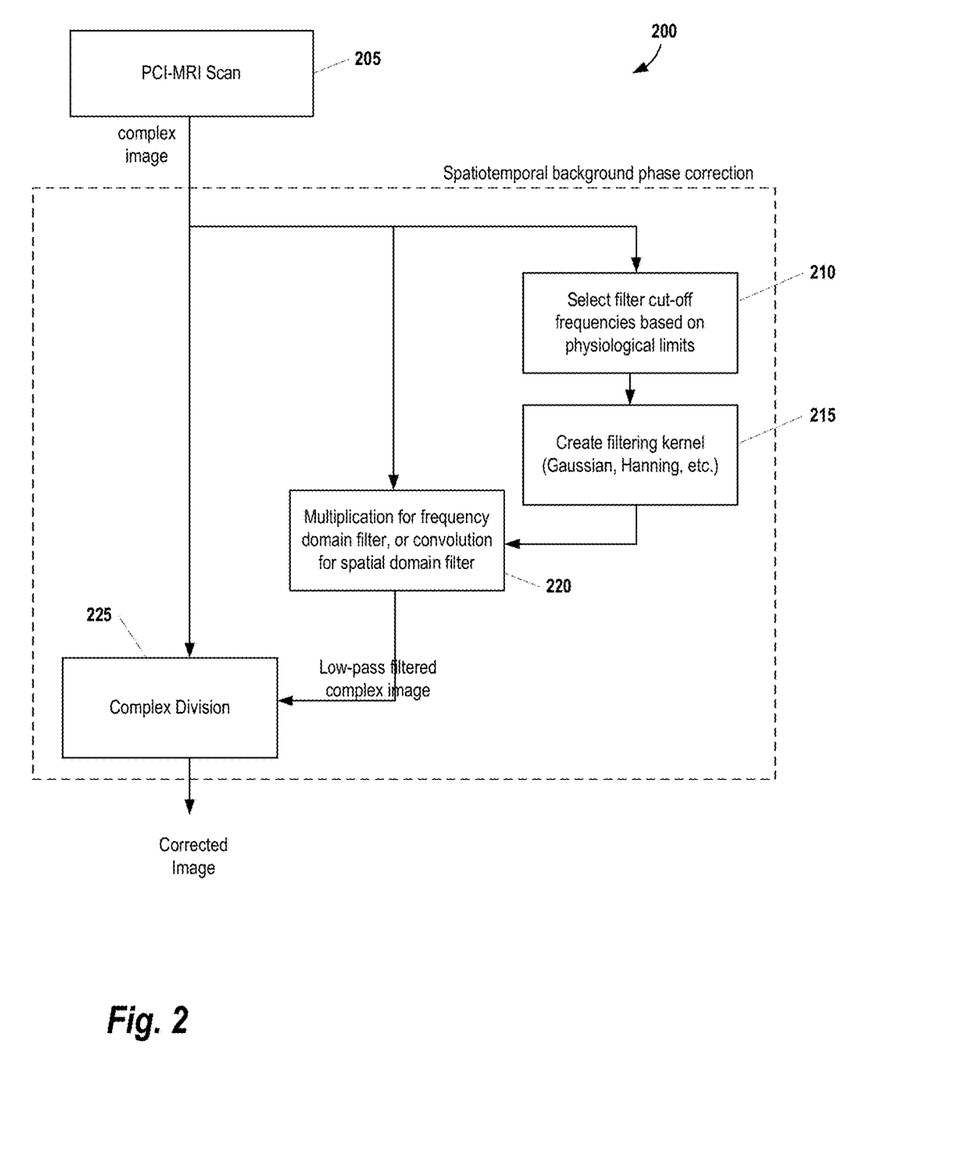
FIG. 2 illustrates a process of spatiotemporal filtering for PC-MRI background phase correction, as may be applied in some embodiments.

FIG. 2 illustrates a process 200 of spatiotemporal filtering for PC-MRI background phase correction, as may be applied in some embodiments. Starting at step 205 a PC-MRI scan is performed to acquire a complex image using an MRI system (see, e.g., FIG. 1). As is generally understood in the art, PC-MRI is a noninvasive technique with which flow can be measured accurately with flexible spatial and temporal resolution. PC-MRI is most commonly performed in 2 spatial dimensions and 1 temporal dimension (i.e., 2D slice with multiple time points in the cardiac cycle), but it is also possible to perform PC-MRI in 3 spatial dimensions and 1 temporal dimension (i.e., a 3D volume with multiple time points in the cardiac cycle). For the latter case, the spatiotemporal background phase correction approach shown in FIG. 2 can be directly extended to the additional spatial dimension. In principle, this could be additionally extended to the velocity encoding dimension for acquisitions with multiple velocity encoding factors.

Continuing with reference to FIG. 2, at steps 210 and 215, filters are generated by first selecting filter cut-off frequencies and then generating a filtering kernel based on those frequencies. Each filter cutoff frequencies in the spatial domain may be set, for example, as a function of the diameter, in pixels, of the largest vessel of interest.

To illustrate how the filter cut-off frequencies may be selected at step 210, consider a frequency domain Gaussian filter for two spatial dimensions and one temporal dimension:

$$F'_{xyt} = F_{xyt} e^{\left(\frac{(\frac{X}{2}-x)^2}{\sigma_x^2} + \frac{(\frac{Y}{2}-y)^2}{\sigma_y^2} + \frac{(\frac{T}{2}-t)^2}{\sigma_t^2}\right)} \quad (1)$$

Here, $F_{xyt}$ is the original 3D image, $F'_{xyt}$ is the low-pass filtered 3D image, (x, y) are the spatial coordinates within a matrix size (X, Y), and t is a time within a total of T time points. The standard deviations $\sigma_x$, $\sigma_y$, and $\sigma_t$ correspond to the standard deviations in the respective dimensions x, y and t. For a Gaussian filter, the cutoff frequency in the spatial/temporal domain $\sigma$ is defined as the standard deviation of the frequency response $\sigma_f$, i.e.:

$$\sigma_f = \frac{1}{2\pi\sigma} \quad (2)$$

Equation 2 thus describes the relationship between filter cutoff frequency parameters in the frequency domain and the spatial/temporal domain.

Now, consider the flow profile through a vessel of interest being described by a Fourier series with harmonics n=1:N. In the spatial domain, the cutoff frequency should be smaller than the fundamental Fourier harmonic (n=1) corresponding to the spatial frequency of the largest vessel of interest. More specifically, the wavelength $\lambda$ in pixels of the lowest allowable spatial frequency should correspond to twice the largest vessel lumen diameter in pixels, i.e. $\emptyset=\lambda/2$. From Equation 2, the cutoff frequency in units of 1/pixel can thus be set as $$\sigma_f = \frac{1}{4\pi\phi} \quad (3)$$

Similarly, in some embodiments, the cutoff frequency in the temporal domain can be set to remove everything except bulk motion. For the case of bulk motion due to respiration, the cutoff can be set using Equation 2 with the frequency of the respiratory cycle.

Note that there is already significant attenuation at these cutoff frequencies, so lower values than those estimated above may be more appropriate in practice. A good rule of thumb is a factor of 2. It should also be noted that, although a Gaussian filter has been described herein as an example, the approach described above can be generalized to other spatial window functions (e.g., Hanning, Hamming, etc.) or frequency domain digital filters (e.g., Butterworth, Chebychev, Bessel, etc.).

Continuing with reference to FIG. 2, at step 220, the original complex image is multiplied with frequency domain filter created at step 215 to produce a low-pass filtered complex image. Alternatively, for a spatial domain filter, a convolution is performed at step 220 to yield the low-pass filtered complex image. Then, at step 225, complex division is performed on the original complex image and the low-pass filtered complex image to yield the corrected image.

Figure 3:
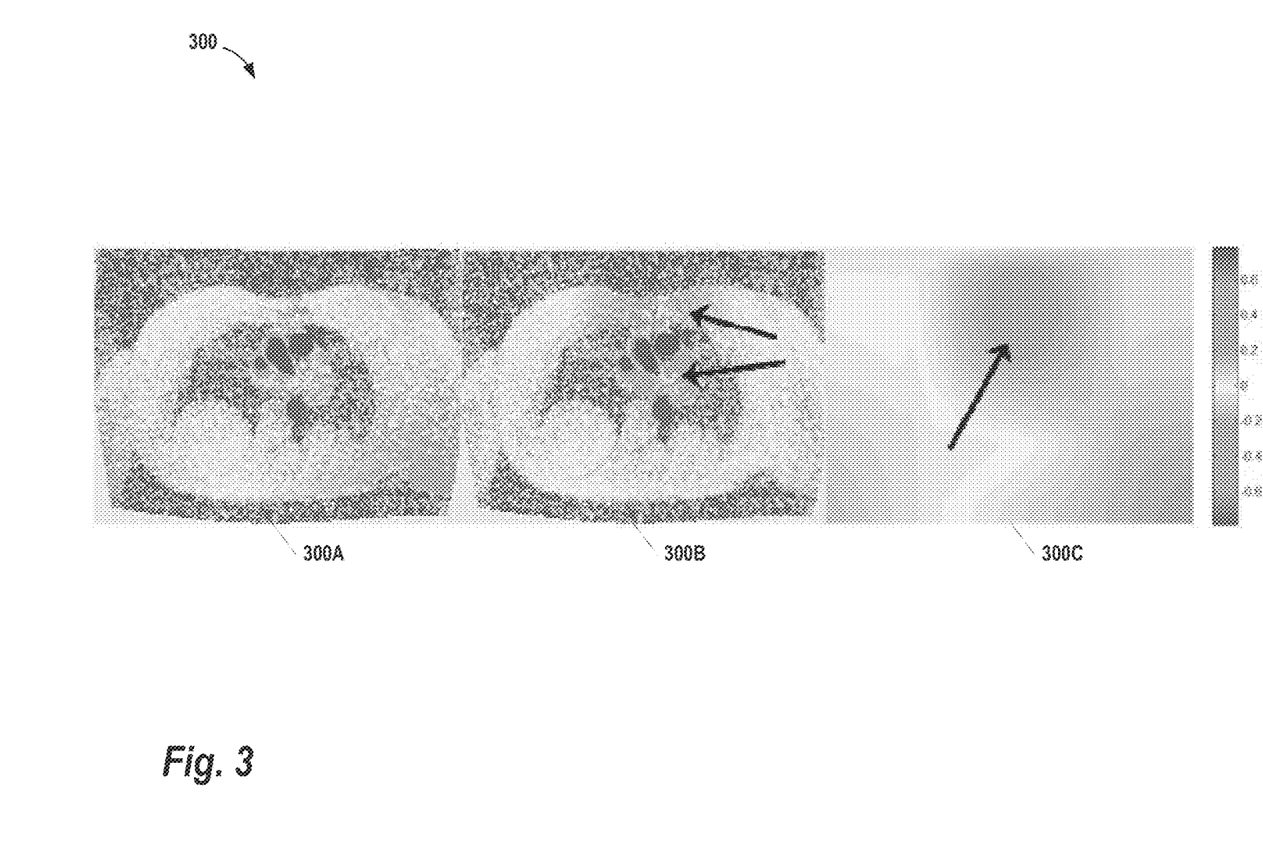
FIG. 3 provides a group of images showing 2D Gaussian low-pass filter with a cutoff set to twice the diameter of the ascending aorta.
Figure 4:
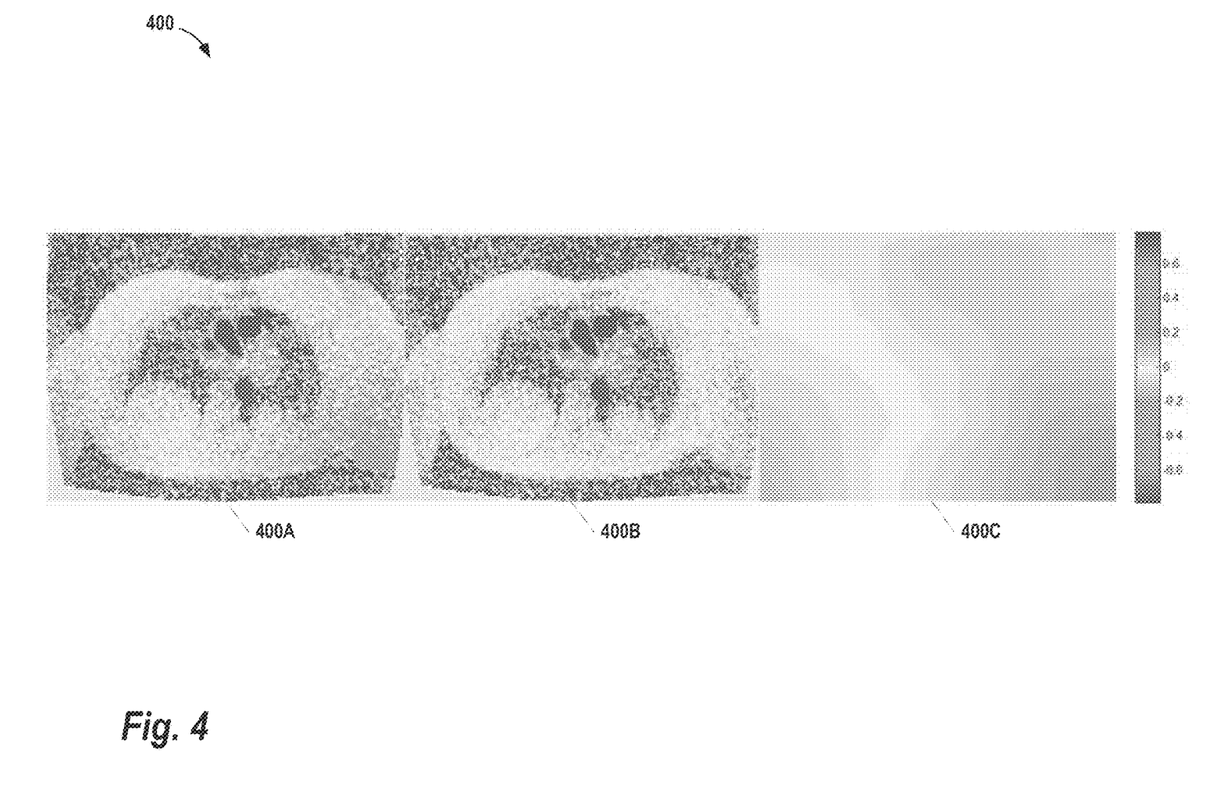
FIG. 4 presents a group of images showing 3D Gaussian low-pass filter with a spatial cutoff set to twice the diameter of the ascending aorta and a temporal cutoff of 6 heartbeats as an estimate of the respiratory cycle.
Figure 5:
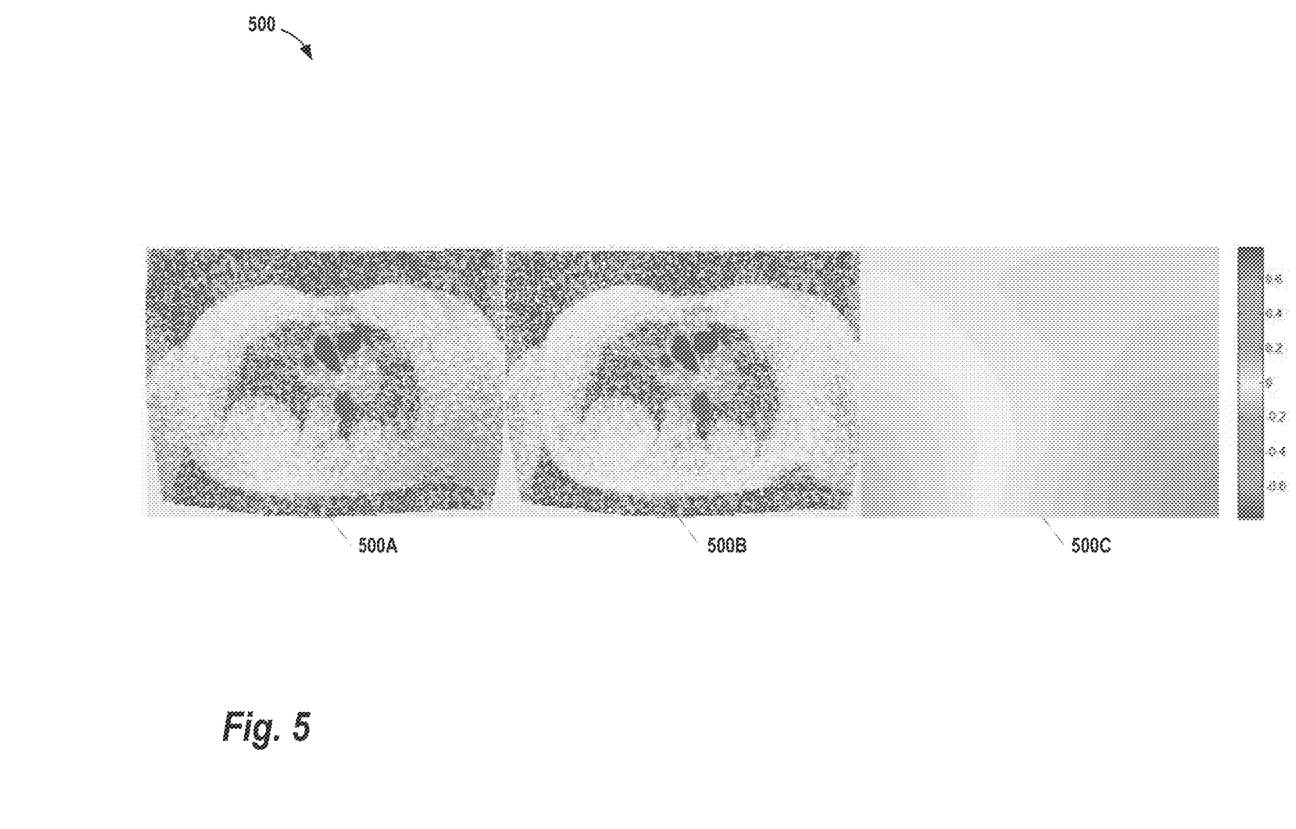
FIG. 5 presents a group of images illustrating a temporal median+2D Gaussian low-pass filter with a spatial cutoff set to twice the diameter of the ascending aorta.

FIGS. 3, 4 and 5 demonstrate the effectiveness of the proposed spatiotemporal filters on an in vivo example. The benefit of including the temporal dimension is clearly evident in FIGS. 4 and 5 compared to FIG. 3. Here the spatial filter cutoff is set to double the diameter of the ascending aorta, and the temporal filter cutoff is set to an estimate of the respiratory cycle. Each image present in FIGS. 3, 4 and 5 is scaled in radians.

FIG. 3 provides a group of images 300 showing 2D Gaussian low-pass filter with a cutoff set to twice the diameter of the ascending aorta, i.e. 30 pixels. Image 300A shows original phase image and a noticeable phase gradient error on the stationary tissue. Image 300B shows a background phase correction using 2D Gaussian low-pass filter, with obvious errors in the background phase correction (as indicated by arrows). Image 300C shows 2D Gaussian low-pass filtered image, illustrating an erroneous estimate of the background phase due to the rapidly flowing blood (as indicated by the arrow).

FIG. 4 presents a group of images 400 showing 3D Gaussian low-pass filter with a spatial cutoff set to twice the diameter of the ascending aorta, i.e. 40 pixels, and a temporal cutoff of 6 heartbeats as an estimate of the respiratory cycle. Image 400A shows the original phase image and a noticeable phase gradient error on the stationary tissue. Image 400B shows the results of applying background phase correction using 3D Gaussian low-pass filter. Image 400C shows a 3D Gaussian low-pass filtered image, showing a good estimate of the background phase.

FIG. 5 presents a group of images 500 illustrating a temporal median+2D Gaussian low-pass filter with a spatial cutoff set to twice the diameter of the ascending aorta, i.e. 30 pixels. Image 500A shows an original phase image and a noticeable phase gradient error on the stationary tissue. Image 500B illustrates the results of performing background phase correction using temporal median+2D Gaussian low-pass filter. Image 500C shows the resultant 2D Gaussian low-pass filtered image, which provides a good estimate of the background phase.

Figure 6:
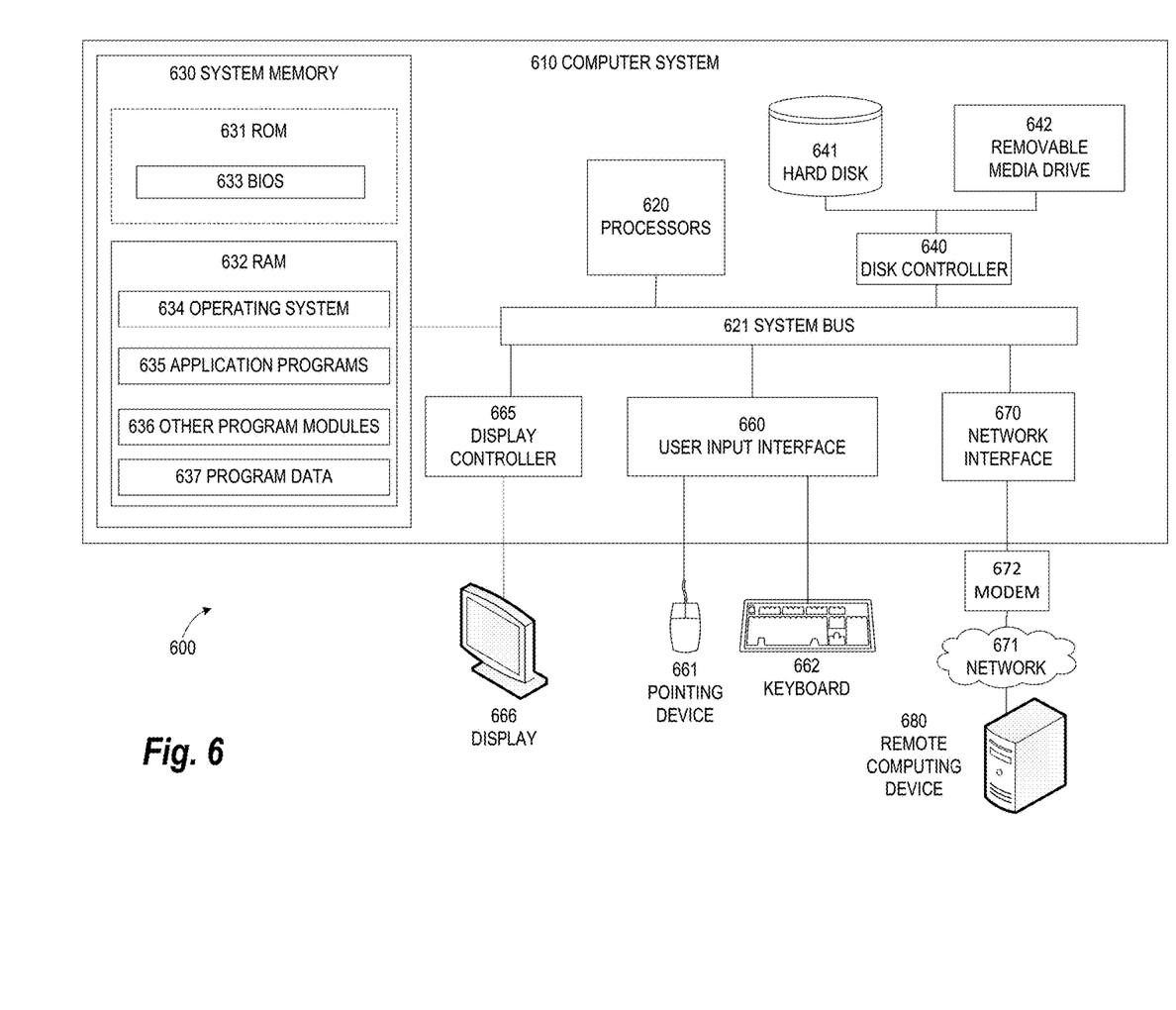
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be used to implement the process 200 described above with respect to FIG. 2. In some embodiments, the computing environment 600 may be used to implement one or more of the components illustrated in the system 100 of FIG. 1. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system (BIOS) 633 containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for performing spatiotemporal background phase correction for phase contrast velocity encoded magnetic resonance imaging, the method comprising:

performing, by a magnetic resonance imaging scanner, a phase contrast magnetic resonance imaging scan of a region of interest within a patient to yield a complex image of the region of interest on a display device;
calculating a plurality of filter cut-off frequencies based on physiological limits associated with the patient;
creating a spatiotemporal filter based on the plurality of filter cut-off frequencies;
applying the spatiotemporal filter to the complex image to yield a low-pass filtered complex image; and
performing complex division using the complex image and the low-pass filtered complex image to yield a corrected image of the region of interest on the display device.

2. The method of claim 1, wherein the plurality of filter cut-off frequencies are calculated based on a flow profile through a vessel of interest present in the complex image,
wherein the magnetic resonance imaging scanner includes a plurality of magnetic coils, configured to create a static base magnetic field in the patient;
a plurality of gradient coils, configured to produce a plurality of position dependent magnetic field gradients superimposed on the static base magnetic field;
wherein the plurality of the position dependent magnetic field gradients include a slice selection gradient magnetic field, a phase encoding gradient magnetic field and a readout gradient magnetic field.

3. The method of claim 2, wherein the filter cut-off frequencies in the spatial domain are specified with a lowest allowable frequency corresponding to twice the diameter of a largest vessel lumen as measured in pixels.

4. The method of claim 2, wherein the filter cut-off frequencies in the temporal domain are specified to remove all motion except for bulk motion of the patient in the region of interest.

5. The method of claim 4, wherein the bulk motion of the patient in the region of interest is due to respiration and the filter cut-off frequencies in the temporal domain are specified using frequency of the patient's respiratory cycle.

6. The method of claim 1, wherein the spatiotemporal filter is in the frequency domain and the complex image is multiplied with a filtering kernel corresponding to the spatiotemporal filter to yield the low-pass filtered complex image.

7. The method of claim 1, wherein the spatiotemporal filter is in the spatial domain and the spatiotemporal filter is applied to the complex image by performing a convolution of a filtering kernel corresponding to the spatiotemporal filter and the complex image.

8. The method of claim 1, wherein the spatiotemporal filter is in the temporal domain and the spatiotemporal filter is applied to the complex image by performing a convolution of a filtering kernel corresponding to the spatiotemporal filter and the complex image.

9. The method of claim 1, wherein the spatiotemporal filter comprises a first filter in the temporal domain and a second filter in the spatial domain which is independent from the temporal filter.

10. The method of claim 1, wherein the phase contrast magnetic resonance imaging scan is performed in a plurality of spatial dimensions and 1 temporal dimension, and the spatiotemporal filter is applied to the complex image in each spatial dimension.

11. An article of manufacture for performing spatiotemporal background phase correction for phase contrast velocity encoded magnetic resonance imaging, the article of manufacture comprising a non-transitory, tangible computer-readable medium holding computer-executable instructions for performing a method comprising:
receiving a complex image of a region of interest within a patient, wherein the complex image of the region of interest is yield from a magnetic resonance imaging scanner and shown on a display device;
generating a spatiotemporal filter using a plurality of filter cut-off frequencies corresponding to physiological limits associated with the patient;
applying the spatiotemporal filter to the complex image to yield a low-pass filtered complex image; and
performing complex division using the complex image and the low-pass filtered complex image to yield a corrected image of the region of interest on the display device.

12. The article of manufacture of claim 11, wherein the plurality of filter cut-off frequencies is selected based on a flow profile through a vessel of interest present in the complex image,
wherein the magnetic resonance imaging scanner includes a plurality of magnetic coils, configured to create a static base magnetic field in the patient;
a plurality of gradient coils, configured to produce a plurality of position dependent magnetic field gradients superimposed on the static base magnetic field;
wherein the plurality of the position dependent magnetic field gradients include a slice selection gradient magnetic field, a phase encoding gradient magnetic field and a readout gradient magnetic field.

13. The article of manufacture of claim 12, wherein the filter cut-off frequencies in the spatial domain are specified with a lowest allowable frequency corresponding to twice the diameter of a largest vessel lumen as measured in pixels.

14. The article of manufacture of claim 12, wherein the filter cut-off frequencies in the temporal domain are specified to remove all motion except for bulk motion of the patient in the region of interest.

15. The article of manufacture of claim 14, wherein the bulk motion of the patient in the region of interest is due to respiration and the filter cut-off frequencies in the temporal domain are specified using frequency of the patient's respiratory cycle.

16. A system for performing spatiotemporal background phase correction for phase contrast velocity encoded magnetic resonance imaging, the system comprising:
a magnetic resonance imaging scanner configured to perform a phase contrast magnetic resonance imaging scan of a region of interest within a patient to yield a complex image of the region of interest on a display device;
a computer comprising an image data processor configured to:
calculate a plurality of filter cut-off frequencies based on physiological limits associated with the patient;
create a spatiotemporal filter based on the plurality of filter cut-off frequencies;
apply the spatiotemporal filter to the complex image to yield a low-pass filtered complex image of the region of interest on the display device; and
perform complex division using the complex image and the low-pass filtered complex image to yield a corrected image of the region of interest on the display device.

17. The system of claim 16, wherein the image data processor is further configured to:
identify a vessel of interest present in the complex image,
wherein the plurality of filter cut-off frequencies is calculated based on a flow profile through the vessel of interest, wherein the magnetic resonance imaging scanner includes
a plurality of magnetic coils, configured to create a static base magnetic field in the patient;
a plurality of gradient coils, configured to produce a plurality of position dependent magnetic field gradients superimposed on the static base magnetic field;
wherein the plurality of the position dependent magnetic field gradients include a slice selection gradient magnetic field, a phase encoding gradient magnetic field and a readout gradient magnetic field.

18. The system of claim 17, wherein the filter cut-off frequencies in the spatial domain are specified with a lowest allowable frequency corresponding to twice the diameter of a largest vessel lumen in the region of interest as measured in pixels.

19. The system of claim 16, wherein the filter cut-off frequencies in the temporal domain are specified to remove all motion except for bulk motion of the patient in the region of interest.

20. The system of claim 19, wherein the bulk motion of the patient in the region of interest is due to respiration and the filter cut-off frequencies in the temporal domain are specified using frequency of the patient's respiratory cycle.

\* \* \* \* \*